United States Patent [19]

Ishida et al.

[11] Patent Number: 5,364,958

[45] Date of Patent: Nov. 15, 1994

[54] PROCESS FOR THE PRODUCTION OF METHYLENE-CROSSLINKED POLYPHENYLENE POLYISOCYANATE

[75] Inventors: Noritoshi Ishida; Zunzi Tashima; Naoki Sato; Michiya Takasaki; Masaaki Iijima; Kazuyuki Kuroda; Kazunari Nitta, all of Omuta, Japan

[73] Assignee: Mitsui Toatsu Chemicals, Incorporated, Tokyo, Japan

[21] Appl. No.: 79,806

[22] Filed: Jun. 22, 1993

[30] Foreign Application Priority Data

Jun. 23, 1992 [JP] Japan ................... 4-164655
Dec. 17, 1992 [JP] Japan ................... 4-337310

[51] Int. Cl.$^5$ ............................. C07C 263/04
[52] U.S. Cl. .......................... 560/359; 528/230; 528/232; 528/266; 528/269; 560/347; 560/352; 560/358
[58] Field of Search ............... 528/230, 232, 266, 269; 560/347, 352, 358, 359

[56] References Cited

U.S. PATENT DOCUMENTS

| | | | |
|---|---|---|---|
| 2,620,349 | 12/1952 | Slocombe | 560/332 |
| 3,219,678 | 11/1965 | Kober et al. | 560/352 |
| 3,234,253 | 2/1966 | Cooper | 560/347 |
| 3,549,504 | 12/1970 | Adica et al. | 203/49 |
| 3,857,871 | 12/1974 | Hatfield, Jr. et al. | 560/352 |
| 4,193,932 | 3/1980 | Yamamoto et al. | 560/347 |
| 4,774,357 | 9/1988 | Keggenhoff et al. | 560/352 |
| 5,179,227 | 1/1993 | Ishida et al. | 560/352 |

Primary Examiner—Samuel A. Acquah
Attorney, Agent, or Firm—Millen, White, Zelano & Branigan

[57] ABSTRACT

The hue of a methylene-crosslinked polyphenylene polyisocyanate continuously produced by the reaction with phosgene in an inert solvent of a polyamine mixture obtained by condensation of aniline and formaldehyde in the presence of an acid catalyst is improved by first removing any residual phosgene followed by heat treatment in the presence of hydrogen chloride gas.

6 Claims, 2 Drawing Sheets 5,364,958

PROCESS FOR THE PRODUCTION OF METHYLENE-CROSSLINKED POLYPHENYLENE POLYISOCYANATE

BACKGROUND OF THE INVENTION

1. Field of the Invention

This invention relates to an improvement in a process for the production of a methylene-crosslinked polyphenylene polyisocyanate. In particular, this invention is concerned with a process for the continuous production of a methylene-crosslinked polyphenylene polyisocyanate which does not contain as impurities acids and hydrolyzable chlorine-containing compounds at high concentrations and is not colored significantly. The term "acids" as used herein means acidic compounds formed upon reaction with an alcohol at room temperature. The term "hydrolyzable chlorine-containing compounds", on the other hand, means impurities which can be hydrolyzed at the boiling point of water to form acidic compounds. The acidic compounds so formed may hereinafter be designated by "HC".

Methylene-crosslinked polyphenylene polyisocyanates have extremely high reactivity and are used for the production of a wide variety of products such as polyurethane foams, elastomers, adhesives and paints.

2. Description of the Related Art

A methylene-crosslinked polyphenylene polyisocyanate (hereinafter abbreviated as "poly-MDI") is industrially produced by reacting a polyamine mixture, which has been formed by condensation of aniline and formaldehyde in the presence of an acid catalyst, with phosgene in the presence of a solvent. In general, diphenylmethane diisocyanate (hereinafter abbreviated as "MDI") is then removed by distillation under reduced pressure, thereby providing a poly-MDI of desired MDI content and viscosity. It is however known that the poly-MDI obtained by the above process contains the acid and HC as impurities and the inclusion of such impurities at high concentrations results in poor reactivity in the production of polyurethane foam.

Many methods have been proposed for lowering the acid and HC contents. Industrially, heat treatment at elevated temperature and reduced pressure is the simplest and most economical method. Poly-MDI is however prone to deterioration in hue during its treatment at elevated temperature or its heating for the removal of MDI. This deterioration in hue then causes coloration upon formation of a polyurethane foam. There is accordingly an outstanding desire for the development of a process which can produce poly-MDI which is not colored significantly and does not contain the acid and HC at high concentrations.

Regarding improvements in the hue of poly-MDI, Japanese Patent Laid-Open No. 58955/1985 discloses a representative method for the removal of color components from poly-MDI. According to this method, poly-MDI is extracted at 180° C. or higher with an aliphatic hydrocarbon having 8 or more carbon atoms so that tar components are eliminated. This method however requires removal of the extraction solvent and treatment of the residual tar components and, accordingly, is not preferred for use in combination with industrial production processes.

Further, a degasification method making use of hydrogen chloride gas is disclosed in U.S. Pat. No. 4,193,932 (Japanese Patent Laid-Open No. 70220/1979). According to this method, hydrogen chloride gas is charged at elevated temperature while phosgene is still present in the mixture. This method however cannot sufficiently lower the acid and HC contents and improve the hue and, moreover, requires a long time. It is therefore not preferred for use in combination with continuous production processes.

SUMMARY OF THE INVENTION

The present inventors have proceeded with an extensive investigation to develop a process suitable for the production of poly-MDI which does not contain the acid and HC at high concentrations and is not colored significantly. As a result, it was found that the acid, HC components and color components in the poly-MDI are composed of the phosgene adducts of carbodiimide compounds formed by the reaction of phosgene with urea compounds produced as by-products upon phosgenation, or dichloroimine derivatives formed by thermal decomposition of phosgene adducts of carbodiimide compounds. Based on the above finding, a further investigation was conducted to develop a method for lowering the contents of the phosgene adducts of carbodiimide compounds as color generating substances. As a result, it has been found that the adducts increase when heated in the presence of phosgene and also that, when subjected to heat treatment in the absence of phosgene in a stream of hydrogen chloride gas, the phosgene adducts are converted to the corresponding hydrochloric acid adducts which are thermally decomposed into the corresponding carbodiimide compounds. The adducts are hence not converted to the acid and HC, and the hue of the poly-MDI is substantially improved, leading to the completion of the present invention.

In one aspect of this invention, there is thus provided a process for continuously producing a methylene-crosslinked polyphenylene polyisocyanate by reacting a polyamine mixture, produced by condensation of aniline and formaldehyde in the presence of an acid catalyst, with phosgene in the presence of an inert solvent, which comprises:

i) removing any residual phosgene which remains after the reaction of the polyamine mixture with phosgene; and ii) subjecting the phosphene-free polyamine mixture to heat treatment in the presence of hydrogen chloride gas.

The process of the present invention can continuously produce a methylene-crosslinked polyphenylene polyisocyanate which has not only low acid and HC contents but also excellent hue and, moreover, is simple and economical. The process is therefore advantageous for the production of methylene-crosslinked polyphenylene polyisocyanates which are industrially produce in large quantities.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENTS

Figure 1:
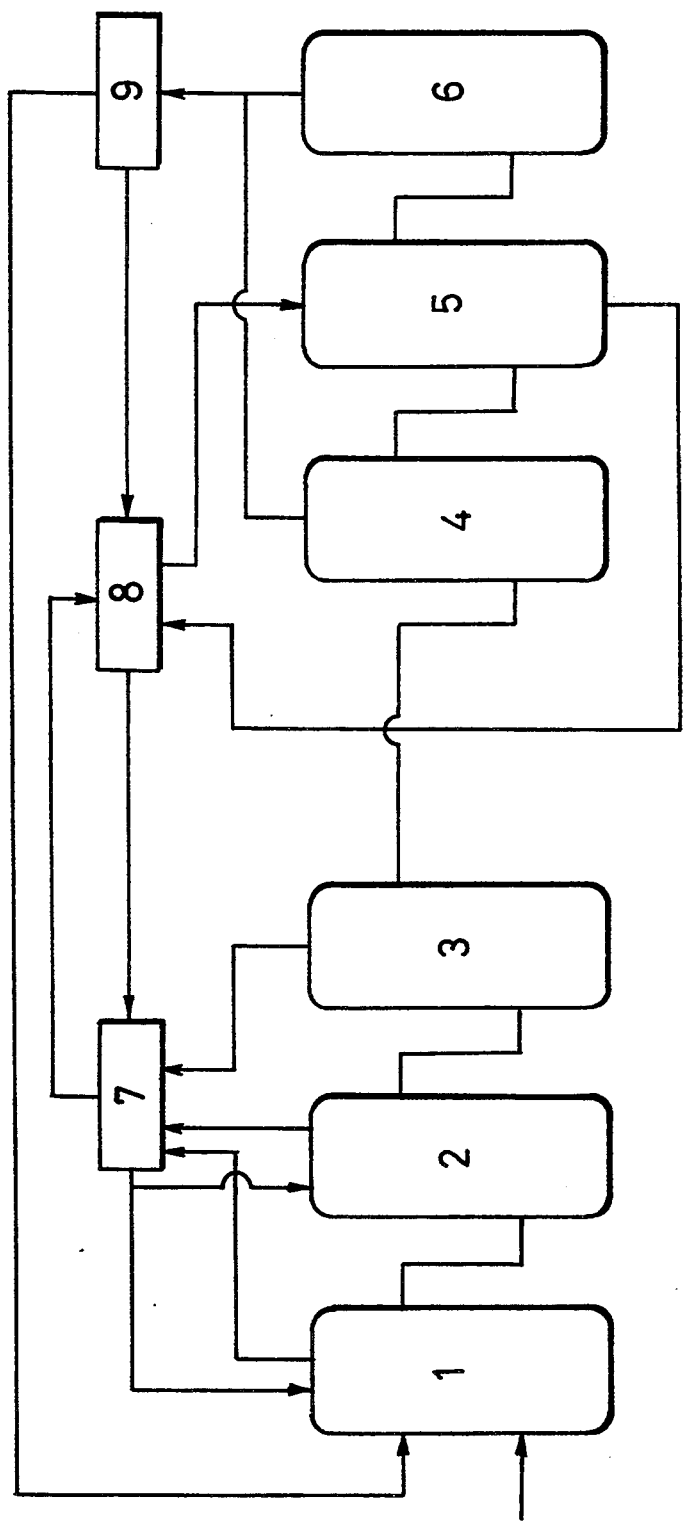
FIG. 1 is a simplified flow diagram of a continuous reactor employed in Example 1.

The polyamine mixture used in the phosgenation reaction is composed of methylene-crosslinked polyphenylene polyamines (hereinafter abbreviated as "poly-MDA") formed by condensation of aniline and formaldehyde in the presence of an acid catalyst. Although the composition of the polyamine mixture varies depending on the aniline/hydrochloric acid/formaldehyde ratio and the condensation temperature, poly-MDA of any composition can be used as a phosgenation reactant in this invention.

No particular limitation is imposed on the inert solvent employed in the phosgenation as long as it is a solvent commonly used in the production of organic isocyanates. Examples of the inert solvent include aromatic hydrocarbons such as toluene and xylene, halogenated hydrocarbons such as chlorotoluene, chlorobenzenes and dichlorobenzenes, esters such as butyl acetate and amyl acetate, and ketones such as methyl isobutyl ketone.

No particular limitation is imposed either on the manner of the phosgenation insofar as it is generally practiced as a continuous process. Any methods can therefore be applied, including the hydrochloride process, the two-stage thermal phosgenation process, and the increased pressure phosgenation process.

The removal of phosgene still remaining after the completion of the phosgenation reaction can be effected preferably by heating the phosgenation reaction mixture at 160° C. or lower. If heated to a temperature higher than 160° C. in the presence of phosgene, the phosgene adducts of carbodiimide compounds are formed in greater quantities so that the subsequent treatment with hydrogen chloride tends to take a longer time. The particularly preferred heating temperature is 140° C. or lower.

As a specific method for the removal of remaining phosgene, it is desired to charge an inert gas such as nitrogen, helium or argon under heating at 100°–140° C. or to heat the phosgenation reaction mixture to the boiling point of the inert solvent under reduced pressure. The latter method has good efficiency.

Subsequent to substantial removal of phosgene, the reaction mixture is subjected to heat treatment in a stream of hydrogen chloride gas, preferably at 60°–160° C. The reaction through which each phosgene adduct is converted to its corresponding hydrochloric acid adduct proceeds faster as the concentration of hydrogen chloride in the reaction mixture becomes higher and the temperature becomes higher. It is preferred to control the temperature as low as possible in order to permit use of a higher hydrogen chloride concentration. Temperatures lower than 60° C. however tend to lower the efficiency. Temperatures ranging from 100° C. to 140° C. are particularly preferred.

The amount of hydrogen chloride gas to be fed to the reaction mixture can be in a range of from 0.01 to 0.1 part by weight per part by weight of the reaction mixture. Although the treatment temperature varies depending on the treatment temperature and also the amount of each phosgene adduct formed during the phosgenation reaction, it is generally desired to set the residence time at 10 minutes when treated at 110° C. and at 20 minutes when treated at 130° C.

The hydrogen chloride treatment can be conducted under pressurized conditions. Use of a higher treatment pressure makes it possible to reduce the amount of hydrogen chloride to be used and also to shorten the treatment time. From the viewpoint of industrial facilities, however, the treatment pressure can be in a range of 0.1–50 kg/cm$^2$G, preferably in a range of 2–10 kg/cm$^2$G.

The time of the treatment with hydrogen chloride is dependent on the treatment temperature, the treatment pressure and the amount of each carbodiimidephosgene adduct formed during the phosgenation reaction, and cannot be determined in a wholesale manner. When the phosgenation and the subsequent removal of remaining phosgene are conducted in a general manner, the treatment temperature generally ranges from 5 minutes to 30 minutes at 90°–140° C. and 3 kg/cm$^2$G.

By the treatment with hydrogen chloride, each phosgene adduct is converted to its corresponding hydrochloric acid adduct and phosgene is formed, pursuant to the following reaction formula:

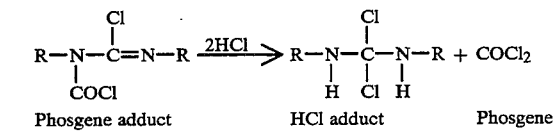

| Phosgene adduct | HCl adduct | Phosgene |

In the reaction mixture treated with hydrogen chloride under pressure, the phosgene formed in the above reaction is dissolved. After removing this phosgene under reduced pressure at 140° C. or lower as needed, desolvation is conducted to obtain crude poly-MDI. Even if the desolvation is conducted without removal of the dissolved phosgene, hue deterioration of the poly-MDI is very little and poses no practical problem. It is however still preferred to remove phosgene.

From the standpoint of lowering the acid and HC contents, it is a preferred embodiment to heat the crude poly-MDI further at 180°–240° C. either after the desolvation treatment or after removal of MDI therefrom. The poly-MDI obtained in accordance with the process of this invention undergoes no substantial deterioration in hue when it is subjected to such heat treatment or is exposed to heat upon removal of MDI.

As specific embodiments of the removal of remaining phosgene and the treatment with hydrogen chloride gas in the present invention, they can be carried out either continuously or batchwise. For industrial practice, continuous processes are preferred from the viewpoints of facilities and labor saving.

The present invention will hereinafter be described in further detail by the following Examples, in which the acid content, HC and hue of each poly-MDI were measured and expressed as will be described next.

Acid content measuring method:

Two grams of each sample were precisely weighed and were then dissolved in 150 ml of a 1:1 mixed solvent of acetone and ethanol. After the sample was reacted at room temperature for 60 minutes, acidic compounds so formed were titrated with a 1/100 (mol/l) methanol solution of potassium hydroxide. The acid content is expressed by the percentage (%) of hydrochloric acid.

HC measuring method:

Each sample was weighed precisely in an amount of 0.4 g, followed by dissolution in 100 ml of a 1:1 mixed solvent of acetone and methanol. The resultant solution was heated on an electric hot plate. Upon initiation of boiling, 60 ml of distilled water were added, followed by hydrolysis for 2 hours. The resulting acidic compounds were titrated with a 1/100 (mol/l) aqueous solution of silver nitrate. The HC of the sample is expressed by the percentage (%) of chlorine.

Hue:

One part by weight of each sample was dissolved in 100 parts by weight of toluene. The absorbance of the resulting solution was measured at 20° C. and 430 nm wavelength. The hue of the sample is expressed by the value of the absorbance.

REFERENTIAL EXAMPLE

Preparation of poly-MDA (methylene-crosslinked polyphenylene polyamine)

In the presence of 46.9 kg of 35% hydrochloric acid, 97.3 kg of 97% aniline and 33.8 kg of a 37% aqueous solution of formaldehyde were subjected to a condensation reaction at 30°–120° C. A 32% aqueous solution of sodium hydroxide (70.7 kg) was added to the reaction mixture to neutralize the solution, followed by the collection of an oil phase. After the oil phase was washed with warm water, the oil phase was distilled under reduced pressure, whereby water and excess aniline were distilled out to obtain 72.6 kg of crude poly-MDA. The crude poly-MDA had the following composition—binuclear condensation product: 76.4% trinuclear condensation product: 16.1%, tetranuclear condensation product: 3.5%, and penta- and higher-nuclear condensation product: 0.7%.

Poly-MDA of the same composition was used in all the Examples and Comparative Example which will be described hereinafter.

EXAMPLE 1

The reactor illustrated in FIG. 1 was used. Fed into a first-stage reaction tank 1 were a 20 wt. % solution of poly-MDA in orthodichlorobenzene (hereinafter abbreviated as "ODCB") at 27.6 kg/hr, phosgene (including recycled phosgene) at 23.7 kg/hr, and ODCB (including recycled ODCB) at 20.8 kg/hr. A reaction mixture drawn by overflow from the first-stage reaction tank 1 was fed to a second-stage reaction tank 2. By jackets and external heaters, the reaction temperature was maintained at 80° C. in the first-stage reaction tank 1 and at 140° C. in the second-stage reaction tank 2. The pressure was maintained at 5.0 kg/cm$^2$G in both the reaction tanks 1,2. The reaction mixture of the second-stage reaction tank 2 was fed at 54.3 kg/hr to a flash tank 3, whereby the pressure of the reaction mixture was allowed to drop to atmospheric pressure and the concentration of phosgene was lowered to 3.6%. The reaction mixture whose phosgene concentration had been lowered to 3.6% was then fed at 49.8 kg/hr to a vacuum degasification column 4. Under the reduced pressure of 115 torr, the reaction mixture was heated at 120° C. with a residence time of 20 minutes (as a result of a gas chromatographic analysis, no phosgene was detected in the reaction mixture). The phosgene-free solution so obtained was then fed to a hydrochloric acid treatment tank 5. While the treatment tank was fed with 0.5 kg/hr of hydrogen chloride, treatment was conducted at 110° C. with a residence time of 10 minutes.

ODCB was caused to evaporate from the thus-treated reaction mixture in a desolvation column 6, followed by the evaporation of 30 wt. % of MDI under reduced pressure of 5 torr at 230° C. in a thin-film distillation equipment.

The absorbance, acid content and HC of the poly-MDI so obtained were 0.04, 120 ppm and 1,000 ppm, respectively.

EXAMPLE 2

Using the same reactor as in Example 1, the procedures of Example 1 were repeated in exactly the same manner except that the temperature of the hydrogen chloride treatment tank and the residence time therein were changed to 130° C. and 20 minutes. The absorbance, acid content and HC of the poly-MDI so obtained were 0.04, 140 ppm and 1,000 ppm, respectively.

EXAMPLE 3

Figure 2:
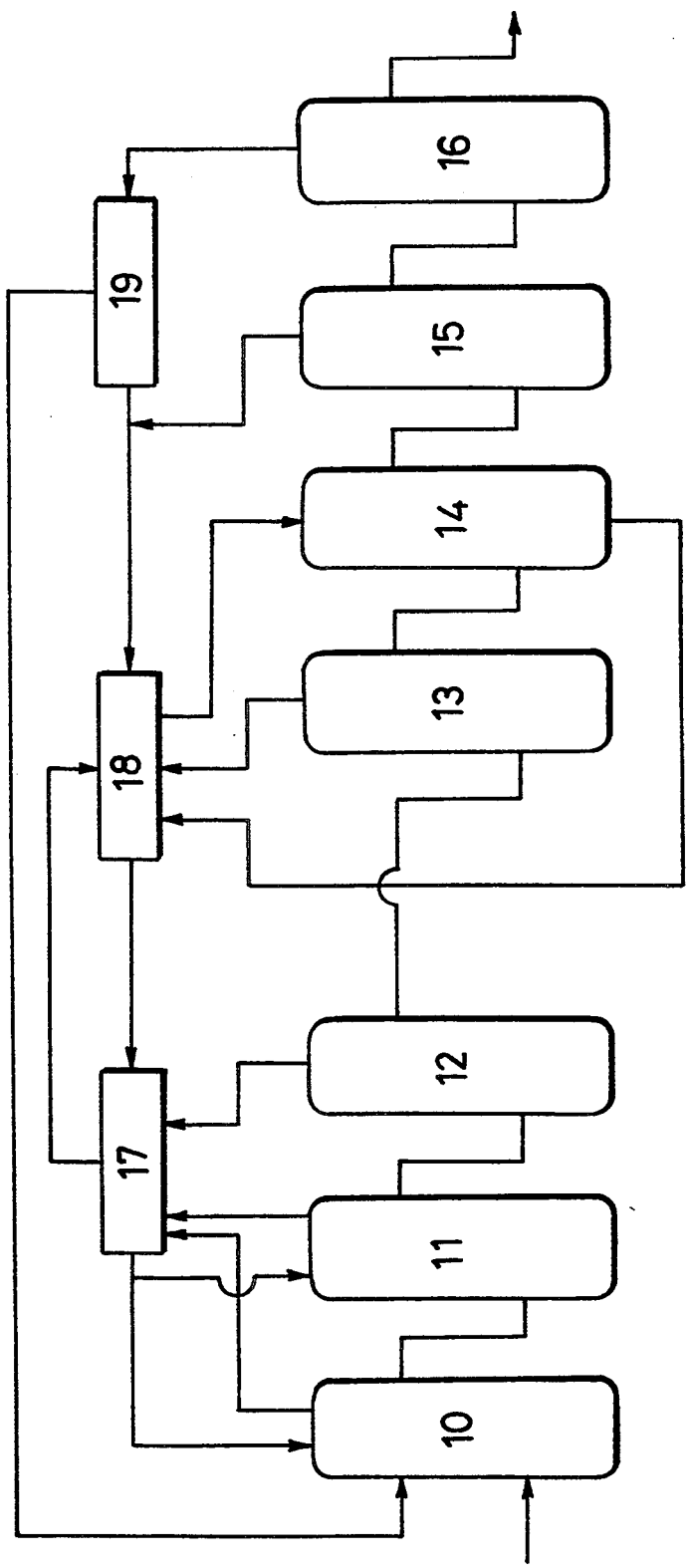
FIG. 2 is a simplified flow diagram of a continuous reactor used in Example 3.

The reactor shown in FIG. 2 was used. Fed into a first-stage reaction tank 10 were a 20 wt. % ODCB solution of poly-MDA at 27.6 kg/hr, phosgene (including recycled phosgene) at 23.7 kg/hr, and ODCB (including recycled ODCB) at 20.8 kg/hr. A reaction mixture drawn by overflow from the first-stage reaction tank 10 was fed to a second-stage reaction tank 11.

By jackets and external heaters, the reaction temperature was maintained at 80° C. in the first-stage reaction tank 10 and at 140° C. in the second-stage reaction tank 11. The pressure was maintained at 5.0 kg/cm$^2$G in both the reaction tanks 10,11. The reaction mixture of the second-stage reaction tank 11 was fed at 54.3 kg/hr to a flash tank 12, whereby the pressure of the reaction mixture was allowed to drop to the atmospheric pressure and the concentration of phosgene was lowered to 3.6%.

The reaction mixture was then fed at 49.8 kg/hr to a vacuum degasification column 13. Under a reduced pressure of 115 torr, the reaction mixture was heated at 120° C. with a residence time of 20 minutes to remove remaining phosgene almost completely (as a result of a gas chromatographic analysis, no phosgene was detected in the reaction mixture).

The phosgene-free solution so obtained was then fed to a hydrochloric acid treatment tank 14. While the treatment tank 14 was fed with 0.5 kg/hr of hydrogen chloride, treatment was conducted at 110° C. with a residence time of 10 minutes under the elevated internal pressure of 3.0 kg/cm$^2$G.

The HCl-treated reaction mixture was fed to a degasification column 15 maintained at 120° C., in which the reaction mixture was treated under the reduced pressure of 115 torr with a residence time of 10 minutes to remove phosgene which had occurred by the treatment with hydrogen chloride. The reaction mixture so treated was then fed to a desolvation column 16, whereby ODCB was removed under reduced pressure to obtain crude poly-MDI.

Using the falling-film evaporator under the conditions of 230° C./5 torr, 30 wt. % of MDI was caused to evaporate from the crude poly-MDI treated and obtained as described above. The absorbance, acid content and HC of the poly-MDI so obtained were 0.03, 110 ppm and 700 ppm, respectively.

EXAMPLE 4

Using the same reactor as in Example 3, the procedures of Example 3 were repeated in exactly the same manner except that the temperature of the hydrogen chloride treatment tank 14 was changed to 130° C. The absorbance, acid content and HC of the poly-MDI so obtained were 0.04, 130 ppm and 800 ppm, respectively.

EXAMPLE 5

Using the same reactor as in Example 3, the procedures of Example 3 were repeated in exactly the same manner except that the treatment pressure and the residence time in the hydrogen chloride treatment tank 14 were changed to 8.0 kg/cm²G and 5 minutes. The absorbance, acid content and HC of the poly-MDI so obtained were 0.03, 110 ppm and 700 ppm, respectively.

COMPARATIVE EXAMPLE 1

Using the same reactor as in Example 1, the procedures of Example 1 were repeated in exactly the same manner except that the vacuum degasification column 4 was not operated, the reaction mixture was fed directly from the flash tank 3 to the hydrogen chloride treatment tank 5 and the temperature of the hydrogen chloride treatment tank was changed to 180° C. The absorbance, acid content and HC of the poly-MDI so obtained were 0.11, 400 ppm and 1,060 ppm, respectively.

We claim:

1. A process for continuously producing a methylene-crosslinked polyphenylene polyisocyanate by reacting a polyamine mixture, which has been formed by condensation of aniline and formaldehyde in the presence of an acid catalyst, with phosgene in the presence of an inert solvent, which comprises:
   i) removing any remaining phosgene subsequent to the reaction of the polyamine mixture with phosgene; and
   ii) conducting heat treatment in the presence of hydrogen chloride gas.

2. In a process for the post treatment with hydrogen chloride gas of a methylene-crosslinked polyphenylene polyisocyanate produced by condensing aniline and formaldehyde in the presence of an acid catalyst to produce a polyamine mixture which is then reacted with phosgene in an inert solvent to produce a solution of the polyisocyanate in the inert solvent, wherein the thus-produced polyisocyanate is heated in the presence of hydrogen chloride gas, the improvement which comprises removing, in the absence of hydrogen chloride gas, residual phosgene from the inert solvent containing the thus-produced polyisocyanate at a temperature of up to 140° C. and thereafter heating the solution in the presence of hydrogen chloride gas at a temperature of 100°–140° C., whereby the hue of the thus-produced polyisocyanate is improved.

3. A process of claim 2, wherein the remaining phosgene is removed at 100° C. to 140° C.

4. A process of claim 2, wherein the heat treatment is conducted in the presence of pressurized hydrogen chloride gas.

5. A process of claim 2, wherein the residual phosgene is removed in an atmosphere of nitrogen, helium or argon.

6. A process of claim 2, wherein the residual phosgene is removed in an atmosphere of nitrogen, helium or argon at a temperature of from 100° C. to 140° C. and the subsequent heat treatment is conducted in the presence of pressurized hydrogen chloride gas.

* * * * *